(12) United States Patent
Barry et al.

(10) Patent No.: US 11,839,418 B2
(45) Date of Patent: Dec. 12, 2023

(54) DEVICE AND METHOD FOR LUNG TREATMENT

(71) Applicant: Uptake Medical Technology Inc., Seattle, WA (US)

(72) Inventors: Robert L. Barry, Kirkland, WA (US); Brian Cran, Seattle, WA (US); Dean T. Corcoran, Seattle, WA (US); Sheldon K. Lee, Seattle, WA (US)

(73) Assignee: Uptake Medical Technology Inc., Seattle, WA (US)

( * ) Notice: Subject to any disclaimer, the term of this patent is extended or adjusted under 35 U.S.C. 154(b) by 446 days.

(21) Appl. No.: 17/022,080

(22) Filed: Sep. 16, 2020

(65) Prior Publication Data

US 2021/0000524 A1   Jan. 7, 2021

Related U.S. Application Data

(60) Continuation of application No. 15/582,765, filed on Apr. 30, 2017, now Pat. No. 10,806,501, which is a
(Continued)

(51) Int. Cl.
*A61B 18/04* (2006.01)
*A61B 1/267* (2006.01)
(Continued)

(52) U.S. Cl.
CPC ............ *A61B 18/04* (2013.01); *A61B 1/2676* (2013.01); *A61B 8/08* (2013.01); *A61M 16/14* (2013.01);
(Continued)

(58) Field of Classification Search
CPC ................ A61B 18/04; A61B 2018/04; A61B 2018/044; A61B 2018/046;
(Continued)

(56) References Cited

U.S. PATENT DOCUMENTS 408,899 A   8/1889   Small
1,719,750 A   7/1929   Bridge et al.
(Continued)

FOREIGN PATENT DOCUMENTS

WO   0011927 A2   3/2000
WO   02069821 A1   9/2002
(Continued)

*Primary Examiner* — Ahmed M Farah
(74) *Attorney, Agent, or Firm* — Batt IP A Law Corporation; Richard Batt

(57) ABSTRACT

This invention relates to the treatment of a patient's lung, for example, a lung exhibiting chronic obstructive pulmonary disease (COPD) and in particular to methods and devices for affecting lung volume reduction, preferably for achieving acute or immediate lung volume reduction following treatment. The lung volume reduction is effected by delivering a condensable vapor at a temperature above body temperature to the desired regions of the patient's lung to damage tissue therein. Blood flow and air flow to the damaged tissue region is essentially terminated, rendering the target region non-functional. Alternative energy sources may be used to effect the thermal damage to the lung tissue.

15 Claims, 5 Drawing Sheets

Related U.S. Application Data continuation of application No. 14/703,580, filed on May 4, 2015, now Pat. No. 9,642,668, which is a division of application No. 13/073,660, filed on Mar. 28, 2011, now Pat. No. 9,050,076, which is a continuation of application No. 11/281,212, filed on Nov. 16, 2005, now Pat. No. 7,913,698.

(60) Provisional application No. 60/648,036, filed on Jan. 27, 2005, provisional application No. 60/628,451, filed on Nov. 16, 2004.

(51) Int. Cl.
*A61B 8/08* (2006.01)
*A61M 16/14* (2006.01)
*A61M 31/00* (2006.01)
*A61N 7/02* (2006.01)
*A61B 18/00* (2006.01)
*A61B 17/00* (2006.01)
*A61N 7/00* (2006.01)

(52) U.S. Cl.
CPC .......... *A61M 31/005* (2013.01); *A61N 7/022* (2013.01); *A61B 2017/00106* (2013.01); *A61B 2018/00285* (2013.01); *A61B 2018/00541* (2013.01); *A61B 2018/00571* (2013.01); *A61B 2018/00994* (2013.01); *A61B 2018/048* (2013.01); *A61B 2218/002* (2013.01); *A61B 2218/007* (2013.01); *A61M 2210/1039* (2013.01); *A61N 2007/0004* (2013.01)

(58) Field of Classification Search
CPC .... A61B 2018/048; A61B 2018/00541; A61B 2018/00571; A61B 2018/00636; A61B 2018/100773; A61B 2018/00791; A61B 2018/00863; A61B 2018/00994; A61B 2017/00017; A61B 2017/00022; A61B 2017/00106; A61B 2017/00115; A61B 1/267; A61B 1/2676; A61M 2210/1025; A61M 2210/1032; A61M 2210/1035; A61M 2210/1039
USPC ...................... 607/42, 96, 105, 107; 128/898
See application file for complete search history.

(56) References Cited

U.S. PATENT DOCUMENTS

| | | |
|---|---|---|
| 3,880,168 A | 4/1975 | Berman |
| 4,026,285 A | 5/1977 | Jackson |
| 4,773,410 A | 9/1988 | Blackmer et al. |
| 4,793,352 A | 12/1988 | Eichenlaub |
| 4,915,113 A | 4/1990 | Holman |
| 4,950,266 A | 8/1990 | Sinofsky |
| 5,006,119 A | 4/1991 | Acker et al. |
| 5,011,566 A | 4/1991 | Hoffman |
| 5,084,043 A | 1/1992 | Hertzmann et al. |
| 5,112,328 A | 5/1992 | Taboada et al. |
| 5,158,536 A | 10/1992 | Michael et al. |
| 5,263,951 A | 11/1993 | Spears et al. |
| 5,331,947 A | 7/1994 | Shturman |
| 5,334,190 A | 8/1994 | Seiler |
| 5,348,551 A | 9/1994 | Spears et al. |
| 5,352,512 A | 10/1994 | Hoffman |
| 5,424,620 A | 6/1995 | Cheon et al. |
| 5,462,521 A | 10/1995 | Brucker et al. |
| 5,500,012 A | 3/1996 | Brucker et al. |
| 5,503,638 A | 4/1996 | Cooper et al. |
| 5,524,620 A | 6/1996 | Rosenschein |
| 5,529,076 A | 6/1996 | Schachar |
| 5,549,628 A | 8/1996 | Cooper et al. |
| 5,562,608 A | 10/1996 | Michael et al. |
| 5,575,803 A | 11/1996 | Cooper et al. |
| 5,591,157 A | 1/1997 | Hennings et al. |
| 5,620,440 A | 4/1997 | Heckele et al. |
| 5,695,507 A | 12/1997 | Auth et al. |
| 5,735,811 A | 4/1998 | Brisken |
| 5,752,965 A | 5/1998 | Francis et al. |
| 5,755,753 A | 5/1998 | Knowlton |
| 5,782,914 A | 7/1998 | Schankereli |
| 5,788,665 A | 8/1998 | Michael |
| 5,800,482 A | 9/1998 | Pomeranz et al. |
| 5,824,703 A | 10/1998 | Clark, Jr. |
| 5,827,268 A | 10/1998 | Laufer |
| 5,913,856 A | 6/1999 | Chia et al. |
| 5,957,919 A | 9/1999 | Laufer |
| 5,964,752 A | 10/1999 | Stone |
| 5,972,026 A | 10/1999 | Laufer et al. |
| 5,986,662 A | 11/1999 | Argiro et al. |
| 5,989,445 A | 11/1999 | Wise et al. |
| 6,032,077 A | 2/2000 | Pomeranz |
| 6,053,909 A | 4/2000 | Shadduck |
| 6,059,011 A | 5/2000 | Giolo |
| 6,083,255 A | 7/2000 | Laufer et al. |
| 6,099,251 A | 8/2000 | Lafleur |
| 6,102,037 A | 8/2000 | Koch |
| 6,113,722 A | 9/2000 | Hoffman et al. |
| 6,130,671 A | 10/2000 | Argiro |
| 6,131,570 A | 10/2000 | Schuster et al. |
| 6,139,571 A * | 10/2000 | Fuller ....................... A61F 7/12 604/113 |
| 6,156,036 A | 12/2000 | Sussman et al. |
| 6,162,232 A | 12/2000 | Shadduck |
| 6,179,805 B1 | 1/2001 | Sussman et al. |
| 6,194,066 B1 | 2/2001 | Hoffman |
| 6,200,333 B1 | 3/2001 | Laufer |
| 6,210,404 B1 | 4/2001 | Shadduck |
| 6,219,059 B1 | 4/2001 | Argiro |
| 6,273,907 B1 | 8/2001 | Laufer |
| 6,283,988 B1 | 9/2001 | Laufer et al. |
| 6,283,989 B1 | 9/2001 | Laufer et al. |
| 6,299,633 B1 | 10/2001 | Laufer |
| 6,300,150 B1 | 10/2001 | Venkatasubramanian |
| 6,312,474 B1 | 11/2001 | Francis et al. |
| 6,327,505 B1 | 12/2001 | Medhkour et al. |
| 6,394,949 B1 | 5/2002 | Crowley et al. |
| 6,398,759 B1 | 6/2002 | Sussman et al. |
| 6,398,775 B1 | 6/2002 | Perkins et al. |
| 6,409,723 B1 | 6/2002 | Edwards |
| 6,411,852 B1 | 6/2002 | Danek et al. |
| 6,458,231 B1 | 10/2002 | Wapner et al. |
| 6,468,313 B1 | 10/2002 | Claeson et al. |
| 6,488,673 B1 | 12/2002 | Laufer et al. |
| 6,493,589 B1 | 12/2002 | Medhkour et al. |
| 6,508,816 B2 | 1/2003 | Shadduck |
| 6,527,761 B1 | 3/2003 | Soltesz et al. |
| 6,575,929 B2 | 6/2003 | Sussman et al. |
| 6,579,270 B2 | 6/2003 | Sussman et al. |
| 6,585,639 B1 | 7/2003 | Kotmel et al. |
| 6,588,613 B1 | 7/2003 | Pechenik et al. |
| 6,589,201 B1 | 7/2003 | Sussman et al. |
| 6,592,594 B2 | 7/2003 | Rimbaugh et al. |
| 6,599,311 B1 | 7/2003 | Biggs et al. |
| 6,610,043 B1 | 8/2003 | Ingenito |
| 6,629,951 B2 | 10/2003 | Laufer et al. |
| 6,652,594 B2 | 11/2003 | Francis et al. |
| 6,653,525 B2 | 11/2003 | Ingenito et al. |
| 6,669,694 B2 | 12/2003 | Shadduck |
| 6,676,628 B2 | 1/2004 | Sussman et al. |
| 6,679,264 B1 | 1/2004 | Deem et al. |
| 6,682,520 B2 | 1/2004 | Ingenito |
| 6,692,494 B1 | 2/2004 | Cooper et al. |
| 6,712,812 B2 | 3/2004 | Roschak et al. |
| 6,719,738 B2 | 4/2004 | Mehier |
| 6,755,794 B2 | 6/2004 | Soukup |
| 6,770,070 B1 | 8/2004 | Balbierz |
| 6,776,765 B2 | 8/2004 | Soukup et al. |
| 6,860,847 B2 | 3/2005 | Alferness et al. |
| 6,885,888 B2 | 4/2005 | Rezai |
| 6,901,927 B2 | 6/2005 | Deem et al. |
| 6,904,909 B2 | 6/2005 | Deem et al. |

(56) References Cited

U.S. PATENT DOCUMENTS

| | | |
|---|---|---|
| 6,907,881 B2 | 6/2005 | Suki et al. |
| 6,911,028 B2 | 6/2005 | Shadduck |
| 6,997,189 B2 | 2/2006 | Biggs et al. |
| 7,022,088 B2 | 4/2006 | Keast et al. |
| 7,027,869 B2 | 4/2006 | Danek et al. |
| 7,031,504 B1 | 4/2006 | Argiro et al. |
| 7,128,748 B2 | 10/2006 | Mooradian et al. |
| 7,136,064 B2 | 11/2006 | Zuiderveld |
| 7,144,402 B2 | 12/2006 | Kuester et al. |
| 7,144,588 B2 | 12/2006 | Nicholas et al. |
| 7,175,644 B2 | 2/2007 | Cooper et al. |
| 7,192,400 B2 | 3/2007 | Campbell et al. |
| 7,198,635 B2 * | 4/2007 | Danek ............... A61B 18/1477 606/41 |
| 7,233,820 B2 | 6/2007 | Gilboa |
| 7,819,908 B2 | 10/2010 | Ingenito |
| 7,913,698 B2 | 3/2011 | Barry et al. |
| 7,993,323 B2 | 8/2011 | Barry et al. |
| 8,322,335 B2 | 12/2012 | Barry et al. |
| 8,585,645 B2 | 11/2013 | Barry et al. |
| 8,734,380 B2 * | 5/2014 | Barry ..................... A61B 18/04 604/23 |
| 8,858,549 B2 * | 10/2014 | Shadduck ............... A61B 18/04 606/41 |
| 10,485,604 B2 * | 11/2019 | Henne .................... A61B 18/04 |
| 2002/0017300 A1 | 2/2002 | Hickle et al. |
| 2002/0077516 A1 | 6/2002 | Flanigan |
| 2002/0111386 A1 | 8/2002 | Michael et al. |
| 2002/0112723 A1 * | 8/2002 | Schuster ........... A61M 15/0045 128/200.24 |
| 2002/0177846 A1 | 11/2002 | Mulier et al. |
| 2003/0181922 A1 | 9/2003 | Alferness |
| 2003/0228344 A1 | 12/2003 | Fields et al. |
| 2004/0031494 A1 | 2/2004 | Danek et al. |
| 2004/0038868 A1 | 2/2004 | Ingenito |
| 2004/0047855 A1 | 3/2004 | Ingenito |
| 2004/0055606 A1 | 3/2004 | Hendricksen et al. |
| 2004/0068306 A1 | 4/2004 | Shadduck |
| 2004/0199226 A1 | 10/2004 | Shadduck |
| 2004/0200484 A1 | 10/2004 | Springmeyer |
| 2004/0244803 A1 | 12/2004 | Tanaka |
| 2005/0016530 A1 | 1/2005 | Mccutcheon et al. |
| 2005/0166925 A1 | 8/2005 | Wilson et al. |
| 2005/0171396 A1 | 8/2005 | Pankratov et al. |
| 2005/0178389 A1 | 8/2005 | Shaw et al. |
| 2005/0203483 A1 | 9/2005 | Perkins et al. |
| 2005/0222485 A1 | 10/2005 | Shaw et al. |
| 2006/0004400 A1 | 1/2006 | Mcgurk et al. |
| 2006/0047291 A1 | 3/2006 | Barry |
| 2006/0130830 A1 | 6/2006 | Barry |
| 2006/0135955 A1 | 6/2006 | Shadduck |
| 2006/0162731 A1 | 7/2006 | Wondka et al. |
| 2006/0200076 A1 | 9/2006 | Gonzalez et al. |
| 2006/0224154 A1 | 10/2006 | Shadduck et al. |
| 2007/0032785 A1 | 2/2007 | Diederich et al. |
| 2007/0036417 A1 | 2/2007 | Argiro et al. |
| 2007/0091087 A1 | 4/2007 | Zuiderveld |
| 2008/0132826 A1 * | 6/2008 | Shadduck ............... A61B 18/04 604/114 |
| 2009/0107491 A1 | 4/2009 | Belson |
| 2010/0256714 A1 * | 10/2010 | Springmeyer ... A61B 17/12104 607/105 |
| 2012/0259271 A1 * | 10/2012 | Shadduck ............... A61B 18/04 604/24 |
| 2019/0350588 A1 * | 11/2019 | Rodriguez ......... A61B 17/1214 |

FOREIGN PATENT DOCUMENTS

| | | |
|---|---|---|
| WO | 03086498 A2 | 10/2003 |
| WO | 2005025635 A2 | 3/2005 |
| WO | 2005102175 A2 | 11/2005 |
| WO | 2006003665 A2 | 1/2006 |
| WO | 2006055695 A1 | 5/2006 |

* cited by examiner

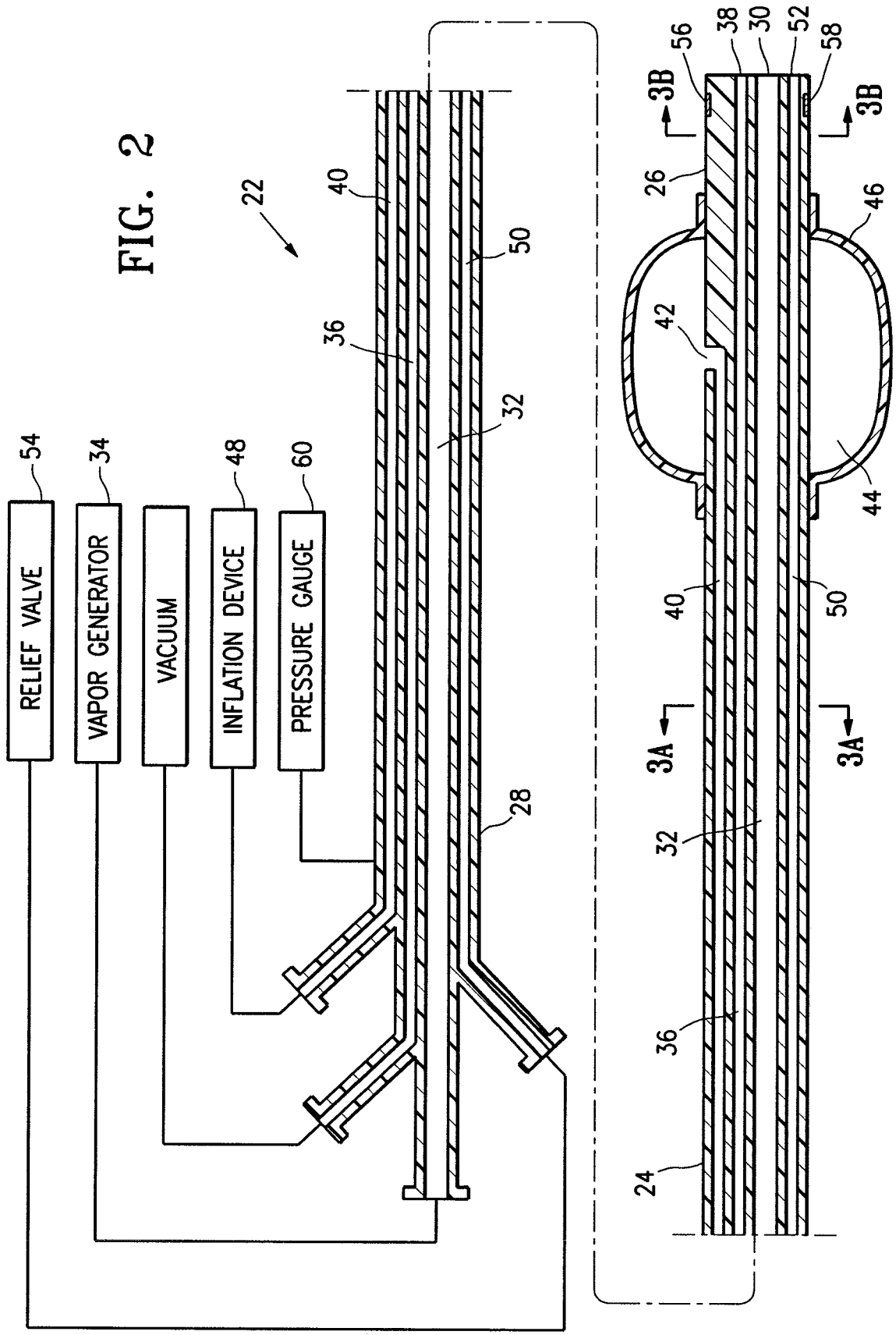

DEVICE AND METHOD FOR LUNG TREATMENT

CROSS-REFERENCE TO RELATED APPLICATIONS

This application is a division of U.S. application Ser. No. 13/073,660, filed Mar. 28, 2011, which is a continuation of U.S. application Ser. No. 11/281,212, filed Nov. 16, 2005, now U.S. Pat. No. 7,913,698; which application claims priority to U.S. Provisional Application No. 60/628,451, filed Nov. 16, 2004, and U.S. Provisional Application No. 60/648,036, filed Jan. 27, 2005, the entire contents of which are incorporated herein by reference.

FIELD OF THE INVENTION

The present invention relates to the treatment of a patient's lung, for example, the treatment of chronic obstructive pulmonary diseases (COPD). In particular this invention relates to systems, devices and methods for affecting lung volume reduction for the treatment of COPD, such as emphysema.

BACKGROUND OF THE INVENTION

Chronic obstructive pulmonary disease (COPD) includes chronic bronchitis and emphysema. COPD is generally characterized by airflow obstruction, which in particular limits the patient's air flow during expiration. Patients with chronic bronchitis have chronic cough with sputum production leading to obstructed expiration. In patients with emphysema, destruction of lung parenchyma can lead to loss of elastic recoil, reduced tethering of the airways, obstruction to expiration, and cough.

Lung function as well as quality of life in patients suffering with a COPD can be improved by reducing a patient's effective lung volume. One way to reduce effective lung volume is by surgically removing diseased portions of the lungs, both to promote expansion of the non-diseased regions, realign a patient's digraph and to redirect inhaled air from diseased portions of lungs into healthier, better functioning lung regions. Surgery often results in effective volume reduction of about 15-30%, which may not be sufficient to cause an appreciable improvement in lung function. Also, conventional lung reduction surgery is traumatic, even when thoracoscopic procedures are employed.

Recently, bronchoscopic approaches for reducing effective lung volume have been proposed. See for example, U.S. Pat. Nos. 6,592,594, 6,679,264, 6,398,775 and 6,610,043; and U.S. Patent Publications 2003/0181922, 2004/0055606, and 2004/0047855. One challenge to achieving effective lung reduction, particularly in emphysematous lungs, is collateral ventilation or collateral pathways.

Accordingly, there is a need for devices, methods and systems for reducing effective lung volume without surgery, and also for reducing lung volume in the presence of collateral pathways. The present invention is directed to meeting these, as well as other, needs.

SUMMARY OF THE INVENTION

This invention relates to the treatment of a patient's lung, for example, the treatment of chronic obstructive pulmonary disease (COPD) and other conditions that can be treated by decreasing a patient's effective lung volume. In particular methods and devices of the invention relate to treatment for affecting lung volume reduction by delivering a thermal damaging agent to a targeted region of a patient's lung so that the region is essentially non-functional.

A method of treating a patient's lung includes delivering a thermal damaging agent to a targeted region of the patient's lung to raise the temperature of the tissue in the region sufficiently high to the extent that blood flow and air flow within the targeted region are terminated. Preferably the thermal damaging agent damages at least one of the group consisting of tissue defining at least in part an air sac of the targeted region, tissue of terminal bronchioles in the targeted region and collateral passageways in the targeted region. The method can also include occluding an airway of the lung through which the thermal damaging agent is delivered at a point proximal to where the thermal damaging agent enters the target region so as to isolate the region and prevent excursions of the thermal damaging agent to areas outside the target region.

One preferred method of treating a patient's lungs includes delivering a condensable vapor at a temperature above body temperature at atmospheric pressures to lung tissue of the target region, particularly the tissue defining at least in part an air sac within the patient's lung.

A device for delivering a thermal damaging agent to a targeted region of the patient's lung to raise the temperature of the lung tissue in the targeted region sufficiently high to render the targeted region essentially non-functional wherein neither blood flow nor air flow occurs within the region. The device for delivering a thermal damaging agent includes an elongate shaft having a proximal portion, a distal portion, and a thermal damaging agent delivering lumen extending within at least a distal portion of the shaft. The device has at least one discharge port in the distal portion of the elongate shaft in fluid communication with the thermal damaging agent delivering inner lumen. A thermal damaging agent generator is in fluid communication with the thermal damaging agent delivery lumen in the elongate shaft and is configured for generating a thermal damaging agent at a temperature above 40° C. to the tissue at the targeted region to render the region essentially non-functional. Preferably the device also includes an occluding member disposed on a distal portion of the shaft to occlude the airway passage proximal to the delivery location of the thermal damaging agent.

In one embodiment the device includes an elongate shaft having a proximal portion, a distal portion, and a vapor delivering inner lumen extending within at least the distal portion of the shaft. The device has at least one discharge port in the distal portion of the elongate shaft in fluid communication with the vapor delivering inner lumen configured to deliver condensable vapor to the target region. A condensable vapor generator is provided in fluid communication with the vapor delivering lumen of the elongate shaft for generating a condensable vapor at a temperature above 40° C. to thermally damage tissue at the targeted region sufficiently to terminate blood flow and air flow to the targeted region. Preferably the device also includes an occluding member disposed on a distal portion of the shaft. The delivered condensable vapor is generally about 40° to 80° C., and preferably is about 50° to about 60° C. The condensable vapor is delivered to the targeted region for a period of about 5 seconds to about 10 minutes, preferably about 5 seconds to about 10 seconds. Suitable liquids for forming the condensable vapor includes water based fluids and perfluorocarbon.

In addition to the treatment of COPD, other conditions can be treated, for example by applying the methods and devices described to pre-cancerous lesions, cancer tumors, or lung nodules. As will be recognized by those skilled in the art, reducing the total volume of a patient's lung, especially an emphysematous lung, can be an effective treatment for COPD.

BRIEF DESCRIPTION OF THE DRAWINGS

FIG. 2 is a longitudinal cross sectional view of the device shown in FIG. 2.

DETAILED DESCRIPTION OF THE INVENTION

Figure 1A:
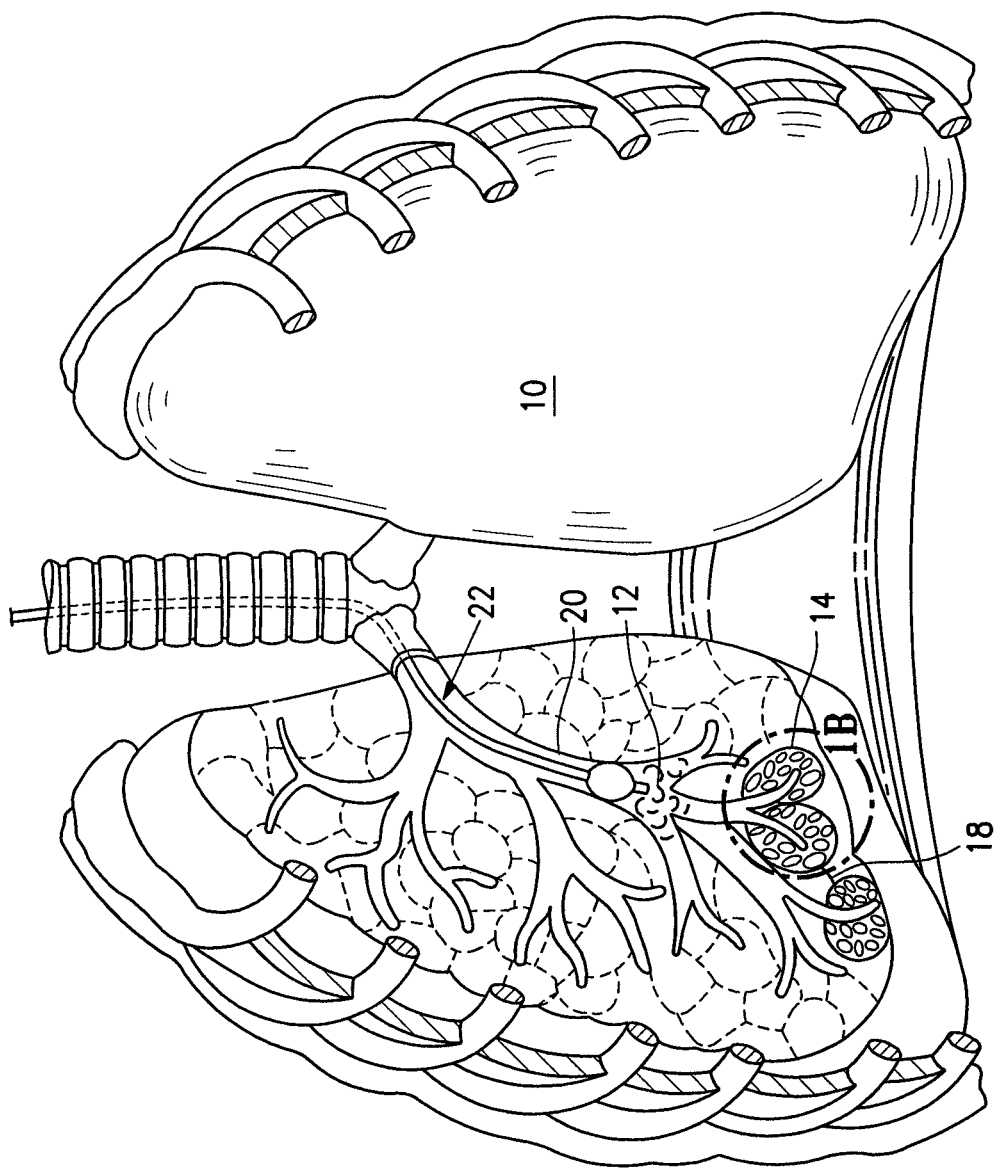
FIG. 1A illustrates a method for treating a patient's lung embodying features of the invention.
Figure 1B:
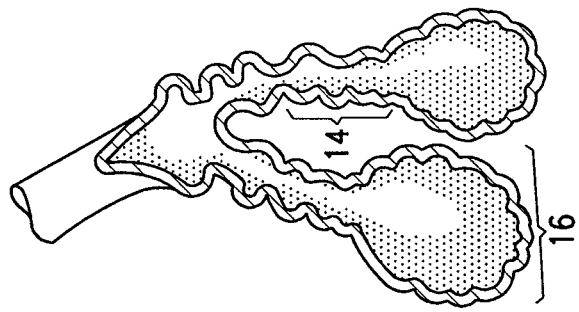
FIG. 1B is an enlarged view of an air sac and alveoli within the patient's lung shown in FIG. 1A.

FIG. 1 illustrates a method for treating a patient's lung 10 embodying features of the invention that includes delivering a condensable vapor 12 to tissue defining an air sac or alveoli 14 within a patient's lung 10 at a temperature above body temperature, preferably about 40° C. to about 80° C., preferably about 50° C. to about 60° C. at atmospheric pressures, so as to damage the tissue of the air sac or alveoli 14, the tissue of terminal bronchioles 16 and tissue of collateral passageways 18. Such tissue damage renders the treated region non-functional in that the blood flow and air flow in the treated region is terminated. The treated region will no longer inflate.

The method includes delivering the condensable vapor through an airway 20 of the lung to the targeted lung region. Preferably the airway 20 is a bronchial passageway such as segmental bronchi, and most preferably a sub segmental bronchi 20.

The condensable vapor 12 serves to rapidly heat the targeted lung region as the vapor 12 is delivered and induces tissue collapse, shrinkage, neointima hyperplasia, necrosis and fibrosis (collectively referred to herein as "bioeffects") of the targeted lung region. Such bioeffects render the target lung region non-functioning.

The method may also include applying a vacuum to the targeted region after delivery of the condensable vapor to further supplement tissue contraction and collapse caused by introduction of the condensable vapor 12. The vacuum generated in the targeted region is about 1 to about 50 mm Hg, preferably about 10 to about 30 mm Hg to effectively collapse the targeted region. The vacuum may also facilitate aspiration of any residual vapor or liquid.

In general the vapor is applied into the targeted region through an airway for anywhere from 5 seconds to 10 minutes or longer. Preferably the condensable vapor is delivered for a short period of time, about 5 seconds to 10 seconds. Because tissue heating and the resulting damage is rapid using energetic vapor, short vapor application times are preferred. In longer procedures, less vapor may be used to cause gradual tissue bioeffects or to treat larger regions or volumes of tissue. Separate procedures may be utilized for separate regions to be treated.

The condensable vapor 12 maybe generated from a liquid, for example, sterile water or other fluids such as perfluorocarbons, having relatively high liquid-gas phase-change temperatures, i.e., boiling points, preferably temperatures well above body temperature. In addition, preferably the condensable vapor 12 is at a temperature sufficient to increase the temperature of the surrounding lung parenchyma to cause damage, for example, above at least 40° C.

In one method of the invention the condensable vapor 12 additionally includes a detectable substance, such as a dye, preferably a biocompatible dye, to detect movement of the condensable vapor 12 and the affected lung regions. Alternatively or in conjunction with the visually detectable substance, diagnostic ultrasound, endoscopic and other conventional visualization techniques are used to monitor the vapor treatment and resulting tissue effects during and after treatment.

In another method embodying features of the invention, the condensable vapor 12 is delivered with microparticulates. Suitable microparticulates include talc, calcium carbonate, antibiotics such as tetracycline and other penicillin derivates, or other particulate substances which induce fibrosis or cause necrosis of the lung tissue.

In another method embodying features of the invention the condensable vapor 12 includes a treatment agent such as an anesthetic or painkillers to alleviate patient discomfort and pain during the treatment. A painkiller, such as lidocane in powder or liquid form, preferably is used or mixed with a condensable vapor 12. Alternatively, pain killers may be delivered to the entire lung, or just to the targeted lung region. Patient preparation with pain medication before, during, and after the procedure is preferred in order to allow treatment using the present invention without the need for general anesthesia.

In another method embodying features of the invention helium or carbon dioxide is delivered in addition to the vapor 12 to lower the temperature of the vapor 12.

A method of the invention includes occluding the airway of a lung proximal to the area where the condensable vapor 12 is delivered. In some embodiments, to prevent condensable vapor from entering and damaging adjacent airways and lung regions, the adjacent airways are filled with a fluid, such as saline. Airways leading to untargeted lung regions may be obstructed to prevent vapor flow therein.

In one method embodying features of the invention high intensity focused ultrasound (HIFU) energy is delivered to damage lung tissue such as the tissue of an air sac or alveoli in the lung. Preferably suitable ultrasound transducers that are capable of delivering high intensity. focused ultrasound (HIFU), generally between about 100-10,000 W/cm$^2$ at a focal spot.

The HIFU energy is delivered in amounts sufficient to cause contraction of lung tissue. Because HIFU can be tightly controlled, the ultrasound energy can be specifically targeted to the epithelium, smooth muscle layer, or collagen layer. Delivery of the HIFU energy can also serve to initiate a healing response (including neointima hyperplasia) which further serves to occlude the passageway. The method can include a wave guide to direct the HIFU sound waves to the intended treatment site. Additionally a vacuum may be applied prior the HIFU to draw down the airway or air sacs.

Alternatively the vacuum may be applied after delivery of the HIFU energy as in the previously discussed embodiment to further supplement tissue contraction and collapse of the terminal bronchioles, air sacs and collateral passageways caused by introduction of the ultrasound energy.

In another embodiment, an ultrasound absorptive material, such as a liquid or gel, can be eluted into the airway of the lung. The absorptive material is heated by the HIFU energy in order to thermally damage the surrounding tissue, resulting in contraction of the airway and or neointima hyperplasia, which will occlude the airway and or damage the air sacs of the lung.

In an alternative embodiment, RF energy can be delivered to a desired location within a patient's lung to damage lung tissue but this usually requires a conductive fluid in contact with the lung tissue for effective ablation.

Figure 3A:
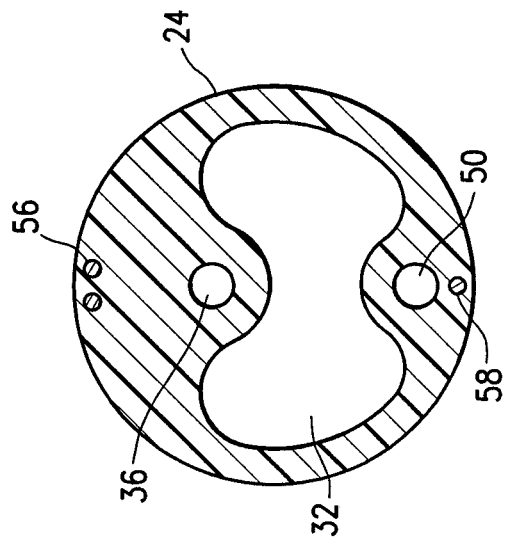
FIG. 3A is a transverse cross sectional view of the device shown in FIG. 2, taken along lines 3A-3A.
Figure 3B:
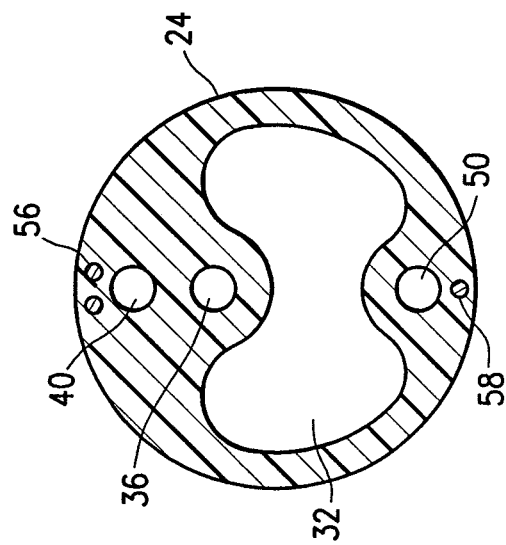
FIG. 3B is a transverse cross sectional view of the device shown in FIG. 2, taken along lines 3B-3B.

FIG. 2 depicts a system 22 embodying features of the invention including an elongate shaft 24 having a distal portion 26 and a proximal portion 28. FIG. 2 is a longitudinal cross sectional view of the elongate shaft 24 and FIGS. 3A and 3B show transverse cross sectional views of the elongate shaft along the lines 3A-3A and lines 3B-3B shown in FIG. 2. The elongated shaft 24 has at least one discharge port 30 in the distal portion 26 of the shaft configured to discharge condensable vapor 12 and a vapor delivering lumen 32 disposed within the elongate shaft 24 in fluid communication with the discharge port 30. A vapor generator 34 is connected to the lumen 32 of the elongate shaft.

The elongate shaft 24 also contains a vacuum lumen 36 which is configured to be connected to a vacuum source for application of a vacuum through vacuum port 38 in the distal portion 26 of the elongate shaft.

The elongated shaft 24 is also provided with an inflation lumen 40 which leads to the inflation port 42. Port 42 opens to the interior 44 of the inflatable balloon 46 which is secured to the distal portion 26 of the shaft. The inflation device 48 may be a conventional syringe. The occluding member 46 is preferably expandable, compliant, and is configured to prevent vapor flow proximal to the location of the member. Suitable balloon materials include silicone or latex. The exterior of the working surface of the inflatable balloon 46 is preferably provided with a knurled or roughened surface to better engage the airway walls and prevent recoil when the condensable vapor is delivered to the target location.

A venting system may be included with the device to ensure that high pressure does not exceed suitable limits. The venting system includes a venting lumen 50 in the shaft 24 which is in fluid communication with the port 52 in the distal end of the shaft 24. The venting mechanism can be a pressure actuated relief valve 54.

The device 22 also includes a temperature sensor 56, for example a thermocouple, located on the distal portion 26 of the elongate shaft 24 to monitor the surrounding temperature. When the temperature is too high, the lung region is brought back to normal temperatures with a lavage or washout procedure to facilitate removal of residual vapor.

The device 22 preferably includes a pressure sensor 58 on the distal portion 26 of the elongate shaft 24 to detect pressure within the targeted lung region. The pressure sensor 58 communicates with a pressure gauge 60 on the proximal portion 28 of the elongate shaft 24. The pressure sensing system may be tied in with the venting system to ensure that preset pressure limits are not exceeded during vapor delivery. Over inflation of the target region could lead to air leaks and tears in the lung pleura.

A suitable flow meter (not shown) may be included to monitor vapor flow to the targeted region of the patient's lung.

Figure 4:
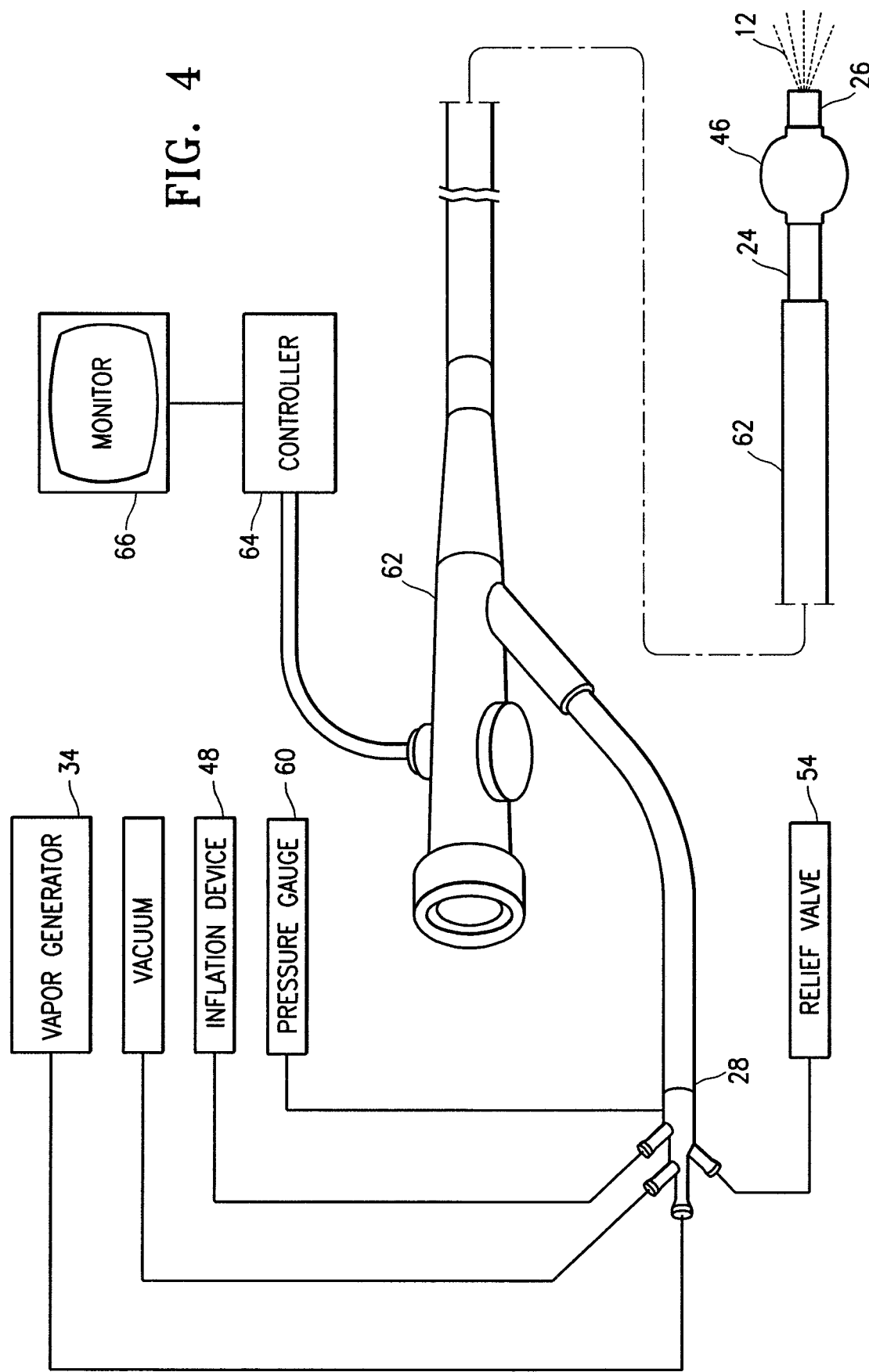
FIG. 4 is an elevational view, partially in perspective, of a system embodying features of the invention.

As shown in FIG. 4 the elongate shaft 24 is configured to be delivered through the working channel (not shown) of an endoscope 62, preferably a bronchoscope. The working channel of the endoscope 62 is preferably between about 1.5 mm and 3.5 mm. The endoscope 62 is connected to an endoscope controller 64 and an endoscope monitor 66. Preferably, the distal portion 26 of the elongate shaft 24 is flexible to facilitate advancement of the elongate shaft in the working channel of the endoscope 62, while the proximal portion 28 is sufficiently rigid for good pushability of the shaft through and out of a distal opening of the endoscope. The distal portion 26 of the shaft 24 is about 1-6 French, the occluding balloon when inflated is larger than the working channel of the endoscope and is typically about 8 French. A suitable endoscope is the Olympus LF-TP bronchoscope.

Alternatively or in addition to the use of the occluding member 46, airways adjacent the delivery airway can be obstructed, for example, with a fluid such as saline. The fluid in the adjacent airways prevents condensable vapor 12 from entering into other lung regions which are not targeted for treatment and prevents damage of the adjacent regions.

Figure 5C:
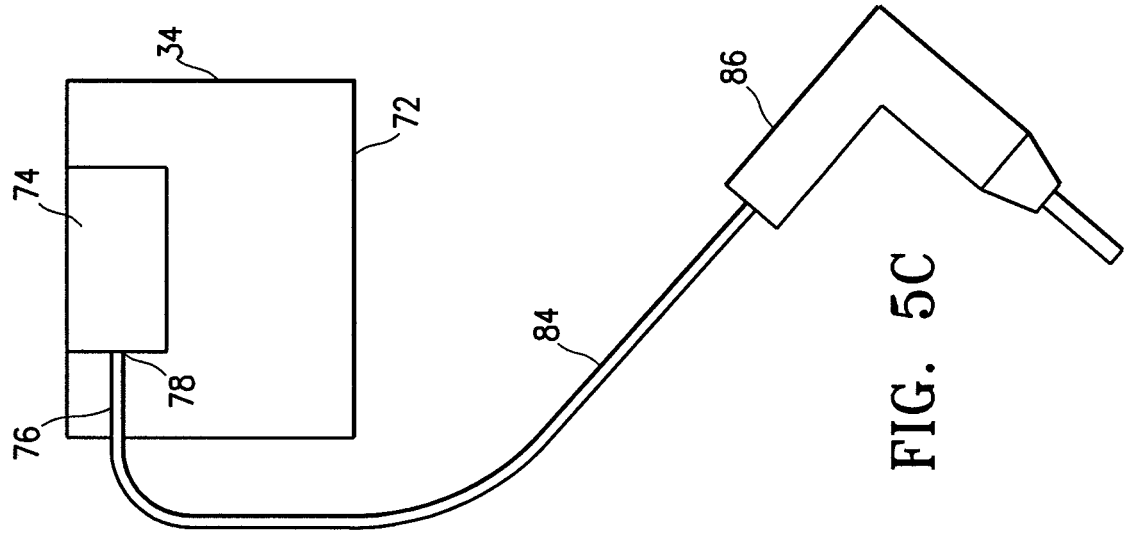
FIG. 5C is an elevational view of a vapor generator connected to the device shown in FIG. 2 which is connected to a hand held operator or pistol grip handle.
Figure 5B:
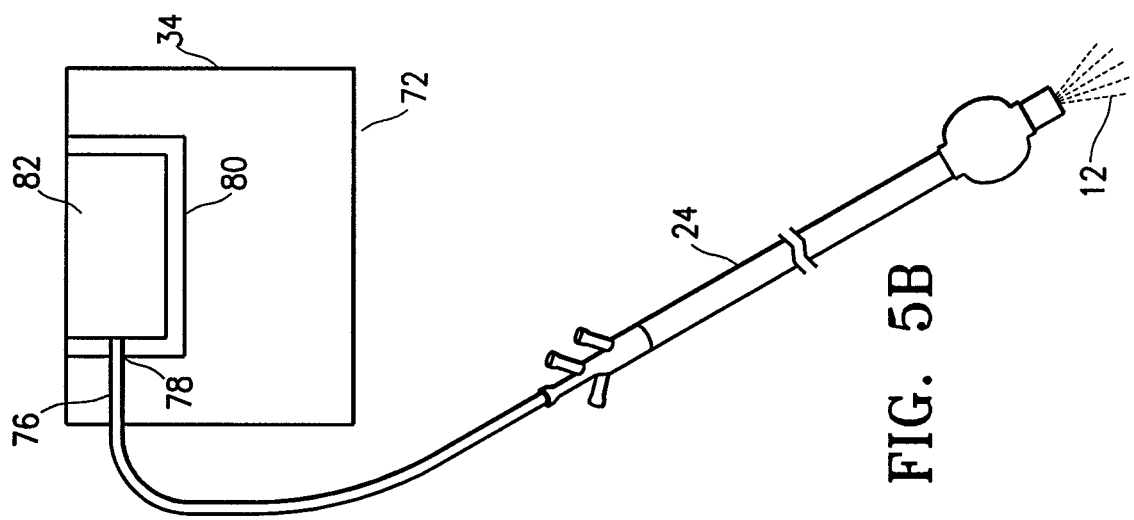
FIG. 5B is an elevational view of a vapor generator connected to the device shown in FIG. 2 which has a cartridge for storing vaporizable fluid.
Figure 5A:
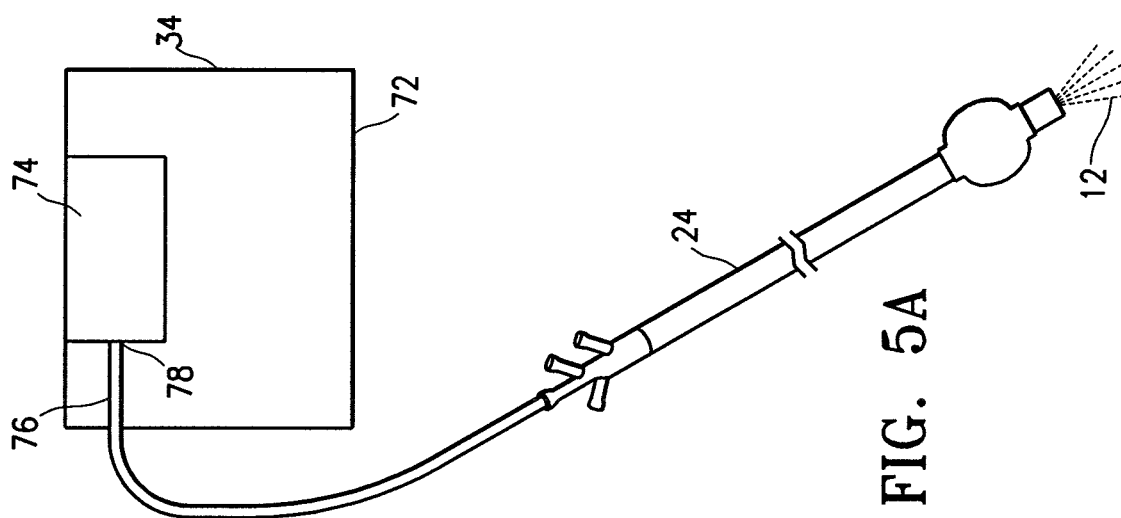
FIG. 5A is an elevational view of a vapor generator connected to the device shown in FIG. 2.

Preferably the vapor generator 34, as shown in FIG. 5A, is external to the elongate shaft 24 and stores the liquid supply. The vapor generator 34 has an outer housing 72 which houses internal structures including a liquid chamber 74 and an inner vapor conduit 76. Liquid may be loaded directly into the liquid chamber. The inner vapor conduit 76 extends from the liquid chamber 74 of the vapor generator 34 to the proximal portion 28 of the first lumen 32 and receives the condensable vapor 12 from the liquid chamber 74 a via an inlet port 78. The vapor generator 34 couples to the elongate shaft 24 via a luer fitting or similar mechanism. The liquid chamber 74 has heating elements such as resistive heating elements, or a RF heater or the like for vaporizing liquid inside the liquid chamber to a condensable vapor. When the liquid is vaporized, the vapor travels from the liquid chamber 74 through the inner vapor conduit 76 and exits into the proximal portion of the vapor lumen 32 of the elongate shaft 24 of the device.

Alternatively, as shown in FIG. 5B the vapor generator includes a cartridge compartment 80 which receives a cartridge 82 in fluid communication with the lumen 32 and containing a predetermined amount of liquid for vaporizing. The cartridge 82 is configured to preferably snap-fit into the compartment 80. When the vapor generator 34 is activated the fluid in the cartridge 82 is heated to a vapor. The condensable vapor 12 is then delivered to the proximal end of the first lumen 32. A predetermined volume or amount of vapor pressure to be delivered to a patient's lung 10 can be determined or calculated based on diagnostic evaluations or parameters of the patient before the treatment procedure, such as forced expiratory volume (FEV) or other lung function and capacity indicators.

In one embodiment, the vapor generator 34, as shown in FIG. 5C has an inner vapor conduit 76 which extends into a generator tube 84. The generator tube 84 connects to a pistol grip handle 86 which is configured to couple to the proximal portion 28 of the elongate shaft. The pistol grip handle 86 can be used to activate heating of the vapor 12 within the liquid chamber 74 of the vapor generator 34. The condensable vapor travels from the vapor generator 34 to the pistol grip 86 and into the elongate shaft 24.

Alternatively, the vapor generator 34 can be disposed within the elongate shaft 24. The heating elements, for example an RF electrode or emitter such as a helical coil, may be embedded within the wall of the shaft, surrounding the lumen 32. The heater may be used as an alternative to the vapor generator 34 or to augment or further control the temperature of the vapor leaving the discharge port 30 from lumen 32.

Preferably, the elongate shaft 24 of the device 22 is heat insulated to avoid overheating of the elongate shaft 24 inside the endoscope 62. In one embodiment the elongate shaft 24 contains a liquid lumen (not shown) and a cooling fluid is delivered within this lumen to prevent overheating.

The condensable vapor 12 is a substance which is capable of rapidly heating a region of the lung to render the target region non-functioning where there is little or no blood flow or air flow within the region. Suitable condensable vapors 12 are selected from the group consisting of condensable vapors from aqueous based fluids, for example, sterile water, saline, contrast fluid, and other fluids such as perfluorocarbons, liquid antibiotics, and other liquids having high liquid-gas phase-change temperatures, i.e., boiling point, preferably above body temperature. In addition preferably the condensable vapor 12 is at a temperature sufficient to increase the temperature of the tissue at the target site to cause tissue damage.

In another embodiment of the invention the condensable vapor 12 includes a detectable substance, such as a dye or a biocompatible dye, to allow the physician to visually track progress of treatment and which lung regions have been treated. Alternatively or in conjunction with the visually detectable material, diagnostic ultrasound, endoscopic and other conventional visualization techniques are used to monitor the condensable vapor treatment and resulting tissue effects during and after treatment.

In yet another embodiment the condensable vapor 12 comprises a treatment agent such as a pain-numbing substance or painkillers to alleviate patient discomfort and pain during the treatment. A painkiller, such as lidocane in aqueous powder or liquid form, preferably is used or mixed with a condensable vapor 12. Alternatively pain killers are delivered to the entire lung, or the targeted lung region. Preferably patient preparation with pain medication before, during, and after the procedure is preferred in order to allow treatment using the present invention without the need for general anesthesia. The device can include a drug delivery lumen in fluid communication with a drug delivery port in the distal portion of the elongate shaft. Painkillers or other drugs can be delivered to the desired area through the optional drug delivery lumen.

In yet another embodiment the elongate shaft 24 of device 22 has a helium or carbon dioxide delivery lumen (not shown) for delivering helium or carbon dioxide in addition to the vapor 12 to lower the temperature of the condensable vapor 12.

While particular forms of the invention have been illustrated and described herein, it will be apparent that various modifications and improvements can be made to the invention. Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is therefore intended that this invention be defined by the scope of the appended claims as broadly as the prior art will permit.

Terms such as "element", "member", "device", "section", "portion", "component", "means", "steps" and words of similar import when used herein shall not be construed as invoking the provisions of 35 U.S.C § 112(6) unless the following claims expressly use the terms "means" or "step" followed by a particular function without reference to a specific structure or action. All patents and all patent applications referred to above are hereby incorporated by reference in their entirety.

What is claimed is:

1. A method for ablating a lung nodule comprising:
navigating a vapor delivery catheter to a location proximal a targeted region encompassing the lung nodule; and
delivering a condensable vapor from the delivery catheter into the targeted region sufficient to ablate the lung nodule, wherein the condensable vapor is delivered at a temperature of at least 40 degrees C. and between 5 seconds and 10 minutes.

2. The method of claim 1 wherein the step of delivering comprises delivering a predetermined amount of the condensable vapor to the targeted region.

3. The method of claim 2 wherein the predetermined amount of condensable vapor comprises a biocompatible dye.

4. The method of claim 3 further comprising detecting or monitoring the ablation by visually observing the dye moving in the targeted region.

5. The method of claim 1, further comprising applying a focused ablation energy to the targeted region.

6. The method of claim 5, wherein the focused ablation energy comprises HIFU.

7. The method of claim 6, further comprising occluding an airway proximal to the area where the condensable vapor is delivered and such that the condensable vapor flows throughout the targeted region.

8. The method of claim 7, wherein the targeted region comprises segmental bronchi and sub-segmental bronchi.

9. The method of claim 1, further comprising delivering a patient preparation medication into the targeted region via said delivery catheter before delivering the condensable vapor.

10. The method of claim 9, wherein the patient preparation medication is a pain-killer or numbing substance.

11. The method of claim 1, wherein the lung nodule is cancerous.

12. The method of claim 1, comprising applying RF ablation to the targeted region.

13. The method of claim 12, further comprising delivering a conductive fluid to the targeted region for effective ablation.

14. The method of claim 1, further comprising applying vacuum to the targeted region.

15. The method of claim 1, wherein the condensable vapor is delivered at a temperature between 50 and 60 degrees C.

* * * * *